United States Patent [19]

Krupnick et al.

[11] Patent Number: 4,918,715
[45] Date of Patent: Apr. 17, 1990

[54] IMAGE LOCATION MARKING DEVICES FOR RADIOGRAPHS, METHOD OF MAKING AND METHODS OF USE

[75] Inventors: Steven B. Krupnick, Philadelphia; Thomas J. McLaughlin, Swarthmore, both of Pa.

[73] Assignee: Webb Research II Corporation, Philadelphia, Pa.

[21] Appl. No.: 345,920

[22] Filed: May 1, 1989

[51] Int. Cl.$^4$ ............................................. H05G 1/28
[52] U.S. Cl. .................................... 378/164; 378/162
[58] Field of Search ................ 378/162, 163, 164, 165

[56] References Cited

U.S. PATENT DOCUMENTS

| | | | |
|---|---|---|---|
| 3,547,121 | 3/1968 | Cherry | 378/164 |
| 3,770,956 | 11/1973 | Johnson | 378/164 |
| 4,181,859 | 12/1977 | Vitalini | 378/164 |
| 4,187,423 | 2/1978 | Ehrhardt | 378/164 |
| 4,691,333 | 9/1987 | Gabriele | 378/164 |

Primary Examiner—Craig E. Church
Attorney, Agent, or Firm—Caesar, Rivise, Bernstein, Cohen & Pokotilow

[57] ABSTRACT

A device for producing plural lines on a film bearing a radiographic image of a portion of the body of a living being to facilitate the location of a part of the being's body within that image. The device comprises a flexible substrate having lines of a radio-opaque material disposed thereon and is made by the application a slurry of a plastisol material and lead particles in the line pattern on the substrate and then drying the slurry. The device is used by applying it over a selected portion of the body of a being, disposing a radiosensitive film under the selected portion of the being's body, exposing the film to radiation, and thereafter developing the film. The resulting radiographic image of the selected portion of the being's body thus has indicator lines crossing it which facilitate the demarcation of a desired portion of that image. In one preferred embodiment the substrate of the device includes plural openings in the lines so that a marking instrument, e.g., a marking pen, can be inserted through at least one selected opening while the device is on the being to mark the body of the being at the selected location.

37 Claims, 4 Drawing Sheets

IMAGE LOCATION MARKING DEVICES FOR RADIOGRAPHS, METHOD OF MAKING AND METHODS OF USE

BACKGROUND OF THE INVENTION

This invention relates generally to devices for facilitating the making of radiographs for medical applications, methods of making such devices and methods of using such devices.

It is a common practice in the taking of medical X-rays to place a preshaped lead marker on a portion of the patient's body to be examined. This marker serves to provide a visual reference point in the resultant X-ray film to facilitate the reading of the X-ray. In particular, one of the most common instances of such a use is in the taking of mammary X-rays. Thus, in such applications a lead ball-like marker is disposed on the patient's nipple and the X-ray taken. The resulting mark which appears on the X-ray film provides the radiologist with a visual indication of the location of the nipple as a reference point to other body structures shown in the developed radiographic image.

Marking devices in the form of plural elongated radioopaque members disposed parallel to one another on a substrate, e.g., a sheet of transparent plastic, have also been used by being disposed across a portion of the patient's body being X-rayed (or CT scanned) to provide a series of parallel lines in the developed image to facilitate the location of desired internal body structure(s) in that image.

While such prior art marking devices are generally suitable for their intended purposes they nevertheless leave something to be desired from the standpoints of ease of use, weight, cost, disposability, etc.

OBJECTS OF THE INVENTION

It is a general object of this invention to provide a device for marking radiographs with indicia which overcomes the disadvantages of the prior art.

It is a further object of this invention to provide a device for marking a radiograph of a being with plural lines to facilitate the location of a desired part of the image of the radiograph.

It is still a further object of this invention to provide a device for marking radiographs with lines which is simple in construction, low in cost, and which is disposable.

It is still a further object of this invention to provide a simple and low cost method of making radiograph marking devices.

It is yet a further object of this invention to provide a method of use of radiographic marking devices to facilitate the location of a desired part of the body of that being from a radiographic image of a portion of the body of the being.

SUMMARY OF THE INVENTION

These and other objects of this invention are achieved by providing a device for producing plural linear indicia on a film bearing a radiographic image of a portion of the body of a being to facilitate the location of a part of the being's body within that image by reference to the indicia. The device comprises a flexible substrate having indicia producing means located thereon for producing the desired indicia when the film is exposed to radiation and developed to create the radiographic image. The indicia producing means comprises carrier means having very fine particles of a radio-opaque material disposed therein. The carrier means with the particles therein is applied on the substrate in a first group of plural rows of lines, with the spacing between the lines of the first group being preselected.

The invention also entails a method of producing the marking device. Thus, that method comprises applying the carrier means with the particles therein to the substrate in the first group of plural rows of lines. In one preferred embodiment the carrier means comprises a slurry of a plastisol material and lead particles. The slurry is silk screened or printed onto the substrate and then heat cured.

The invention also entails a method of using the marking device. Thus, that method entails applying the device over a selected portion of the body of a being, disposing a radiosensitive film or other radiosensitive means under the portion of the being's body, exposing the film or such means to radiation through the device and the portion of the being's body, and thereafter developing the film or producing an image from such means so that a plurality of lines are produced in the radiographic image of the portion of the being's body to facilitate the location of the desired part of the being's body within that image. In one preferred embodiment the substrate of the device includes plural openings in the lines so that a marking instrument, e.g., a marking pen, can be inserted through at least one selected opening while the marking device is on the being to mark the body of the being at the selected location.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
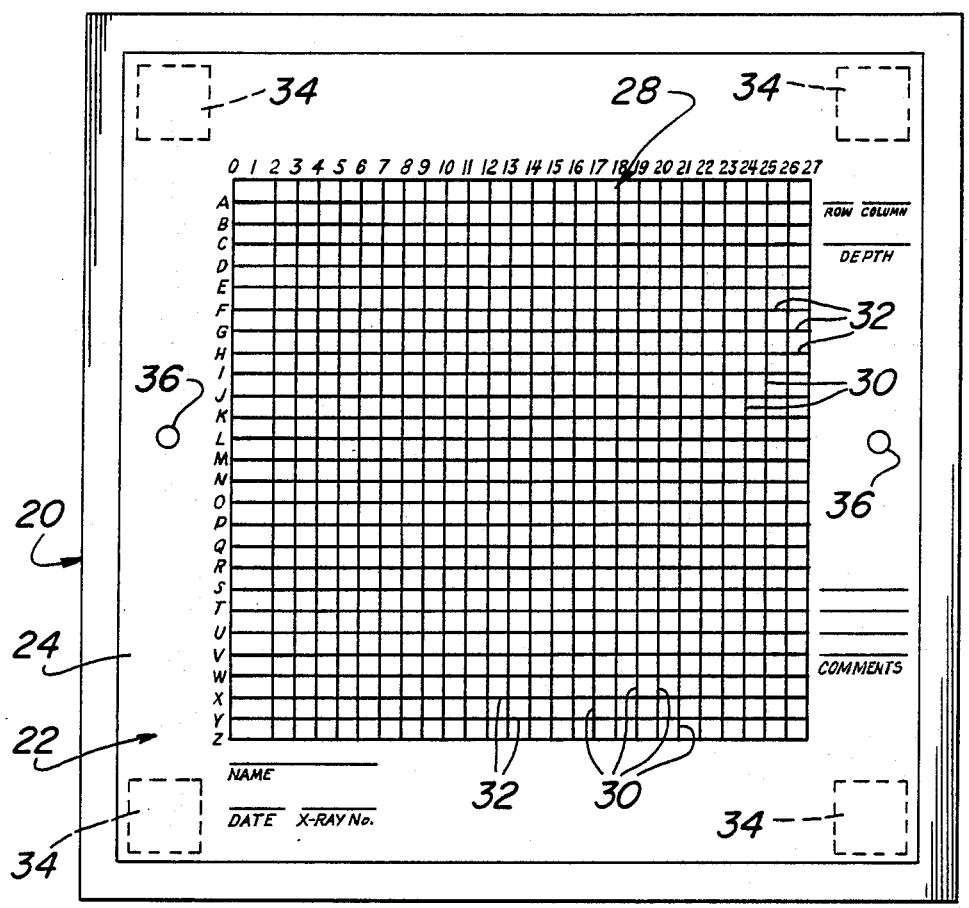
FIG. 1 is a top plan view of one embodiment of a radiographic marker device constructed in accordance with this invention.
Figure 5:
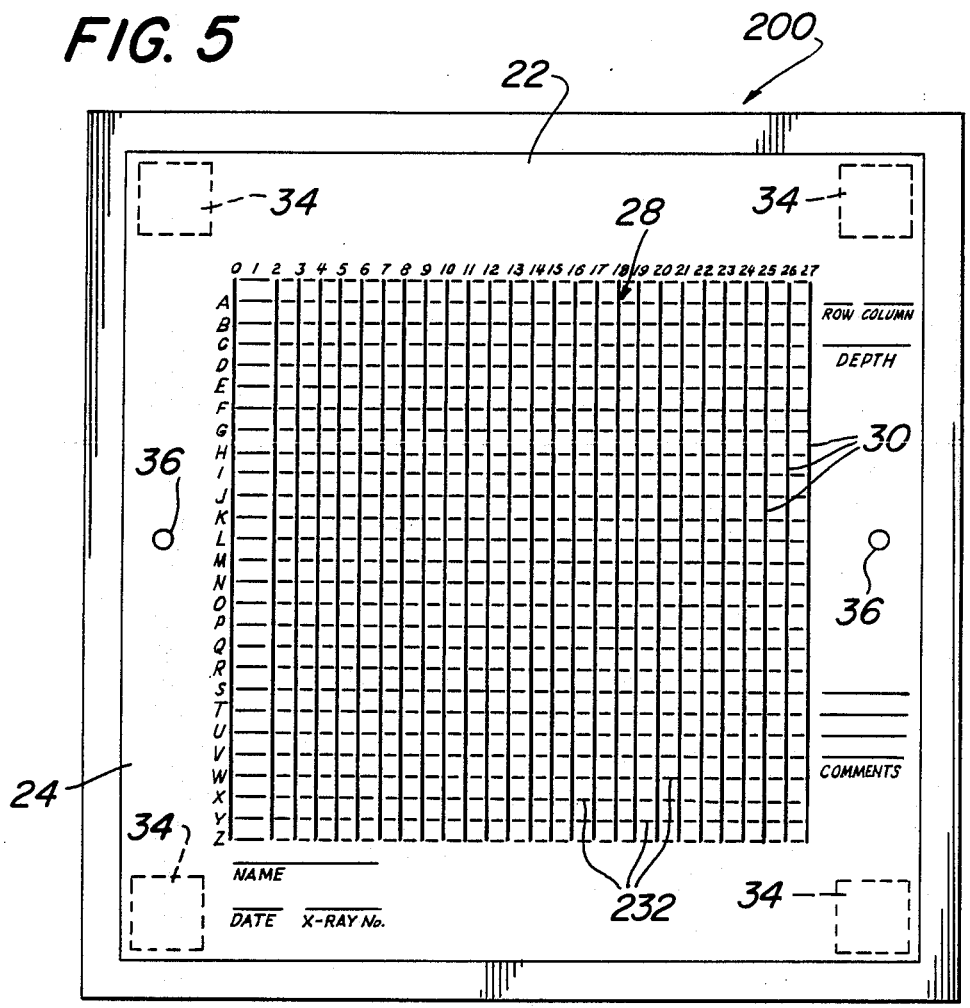
FIG. 5 is a top plan view of another preferred embodiment of a radiographic marker device constructed in accordance with this invention.

Referring now to various figures of the drawing where like reference numerals refer to like parts there is shown at 20 in FIG. 1 a radiographic marker sheet constructed in accordance with one preferred embodiment of this invention. In FIG. 5 there is shown an a alternative radiographic sheet 200 constructed in accordance with a second preferred embodiment of this invention. In the interests of brevity and expediency all common components and features of the two marker sheets 20 and 200 will be given the same reference numerals herein.

Figure 2:
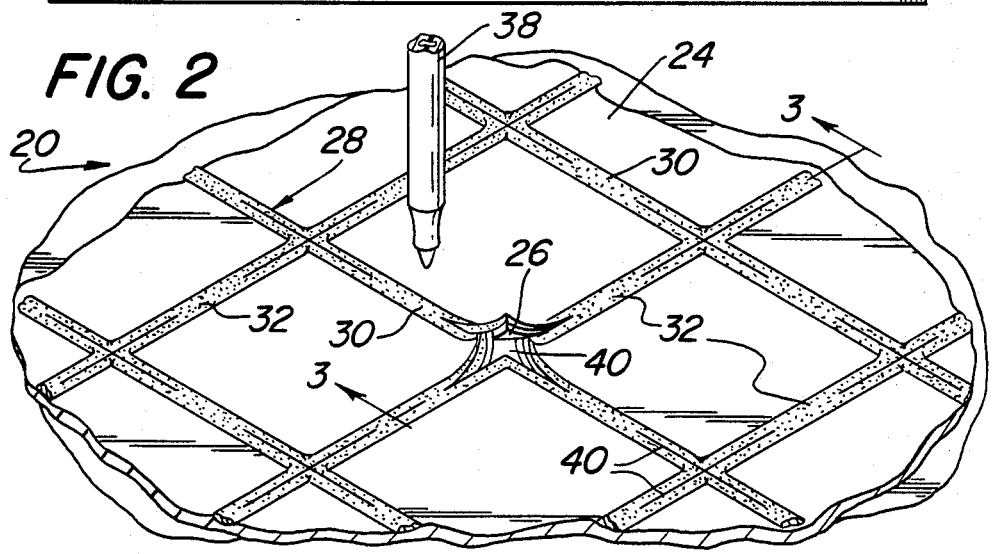
FIG. 2 is an enlarged perspective view of a portion of the marker device shown in FIG. 1 showing one aspect of its manner of use.
Figure 3:
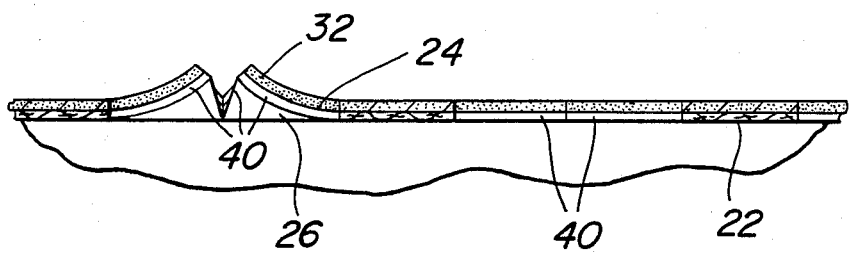
FIG. 3 is an enlarged sectional view taken along line 3—3 of FIG. 2.

Thus, as can be seen clearly in FIGS. 1, 2 and 3 the marker sheet 20 basically comprises a substrate 22 having an upper surface 24 and a lower surface 26. The upper surface 24 includes radiographic indicia image producing means 28 thereon. That means basically comprises a radio-opaque material which has been applied to the substrate's surface in predetermined pattern. In the case of the marker 20 shown in FIG. 1 the image producing means 28 is in a grid-like pattern comprising a first group of parallel vertical lines 30 and a second group of parallel horizontal lines 32. The lines 30 and 32 intersect one another at 90 degree angles.

In accordance with a preferred embodiment of this invention for use with either X-ray imaging or CT (CAT) scanning imaging, the image producing means 28 constitutes a lead filled plastisol, i.e., a slurry of a plastisol carrier and fine lead particles. The plastisol can be any suitable type, such as a liquid dispersion of PVC homopolymers, PVC copolymers, or mixtures thereof, in combination with a plasticizer, such as phthalate ester, as well as other additives. One particularly effective lead filled plastisol is sold by Dennis Chemical Company of St. Louis, Mo. under the designation DENFLEX 9000. That plastisol is a mixture of PVC homopolymers and copolymers, along with a phthalate ester plasticizer, a thickening agent of fumed silica and fine lead particles and has the following characteristics:

| Brookfield Viscosity @ 80° F. | |
| --- | --- |
| 2½ rpm | 3-4 × 20 rpm viscosity |
| 20 rpm | 10,000-15,000 cps |
| Density (lbs/gal) | 39 +/− 1 |
| Durometer (Shore A) | 55-60 |
| % lead (by weight) | 83-86 |

In accordance with a preferred aspect of this invention the lead filled plastisol (slurry) is applied to the substrate in the desired pattern by silk screening (or some other type of printing process). Thereafter, the screened substrate is placed in an oven to be heat cured at approximately 350 degrees F. for approximately 1-3 minutes to cause the plastisol to set.

The substrate 22 bearing the radio-opaque grid-like indicia 28 can be formed of various types of materials. One preferred material comprises spun bonded nylon (100% continuous filament) sheet material, such as that sold under the trademark CEREX (TYPE 23) James River Corporation of Greenville S.C. That material is semi-transparent (somewhat translucent) and has a weight of 0.7 oz. per sq. yd. Other suitable, inexpensive, silk-screenable, flexible sheet materials can be used as the substrate 22, if desired.

It must be pointed out at this juncture that this invention is not limited to use with X-ray or CT scanning procedures. Thus, this invention can be utilized in various types of imaging processes, e.g., MRI scanning, PET scanning, etc. In the case of MRI imaging the material forming the linear indicia of this invention merely needs to be capable of producing an image on the film or other medium which will bear the image of the body portion being subjected to the magnetic resonance. Thus, for MRI scanning the preferred "radio-opaque" material is a slurry of plastisol and aluminum particles. For PET scanning, like X-ray and CAT scanning, a slurry of plastisol and lead particles is preferred. Although other radio-opaque material such as, barium or triphenyl bismuth can be used.

The marker device is arranged to be disposed on the portion of the patient's body to be imaged and is held in place thereon via plural patches 34 of adhesive located on the underside surface 26 of the sheet 20. Four patches 34 can be in the four corners as shown or else two patches can be used adjacent each side marginal edge in the center of the sheet. The translucency or semi-transparency of the substrate enables the portion of the patient's body to be seen therethrough to facilitate placement of the marker sheet thereon.

The sheet 20 may also include plural alignment holes 36 (See FIG. 5). The holes 36 enable the radiologist to apply visible marks on the patient's body by inserting the tip of a conventional marking pen 38 therethrough. These marks can be used as alignment marks to enable the repositioning of the sheet on the patient should it be moved. The holes 36 can be two in number (as shown) located adjacent each side marginal edge in the center of the sheet or else can be four in number, one in each corner of the sheet.

As can be seen in FIG. 1 the sheet 20 may also include other indicia thereon. Such indicia may be in the form of numbers and/or letters used to identify the respective lines forming the grid-like pattern 28. If such additional indicia are used they may also be formed of the radio-opaque material forming the grid pattern so that they will appear in the X-ray when it s developed. Other indicia (which may also be radio-opaque) can be provided on the sheet to carry other information, such as direction (e.g., use of the character "L" to signify "left"), patient identity (e.g. "NAME___"), date of the X-ray (e.g., "DATE___"), etc.

Once the marker sheet is in position on the patient and the radiosensitive film (not shown) is disposed under the patient so that the portion of the patient's body to be imaged is interposed between the marker sheet and the film, the film may be exposed to X-ray radiation and then developed. This action will produce a film 50 (see FIG. 4) bearing the image 52 of the body structure within the field of a grid-like pattern having lines 30A and 30B corresponding to and produced by the by the radioopaque lines 30 and 32, respectively, of means 28, thereby expediting the finding/location of any particular body structure within that image.

As can be seen clearly in FIG. 2 the intersection of each of the vertical and horizontal lines 30 and 32, respectively, of the grid pattern 28 is die-cut in a cross pattern to form an opening 40. The openings 40 serve as an access passageway to enable the radiologist or some other personnel to visibly mark the body of the patient at a desired location. For example, if the X-ray is taken to determine the location for a needle biopsy, once the site of the body structure to be tested is located with respect to the grid lines in the developed X-ray film 50 a marking pen 38 may be inserted through the opening(s) 40 in sheet 20 located closest to that site to place a visible mark on the patient. The marker sheet 20 can then be removed and the needle biopsy taken at the marked point any time thereafter.

The embodiment of the marker sheet 200 shown in FIG. 5 differs from the sheet 20 of FIG. 1 in that the transverse lines of sheet 200 are not formed of a radio-opaque material so that they do not show up in the developed film. Thus, in the embodiment 200 the transverse lines (denoted by the reference numeral 232) are formed of any conventional radio transparent ink.

Figure 8:
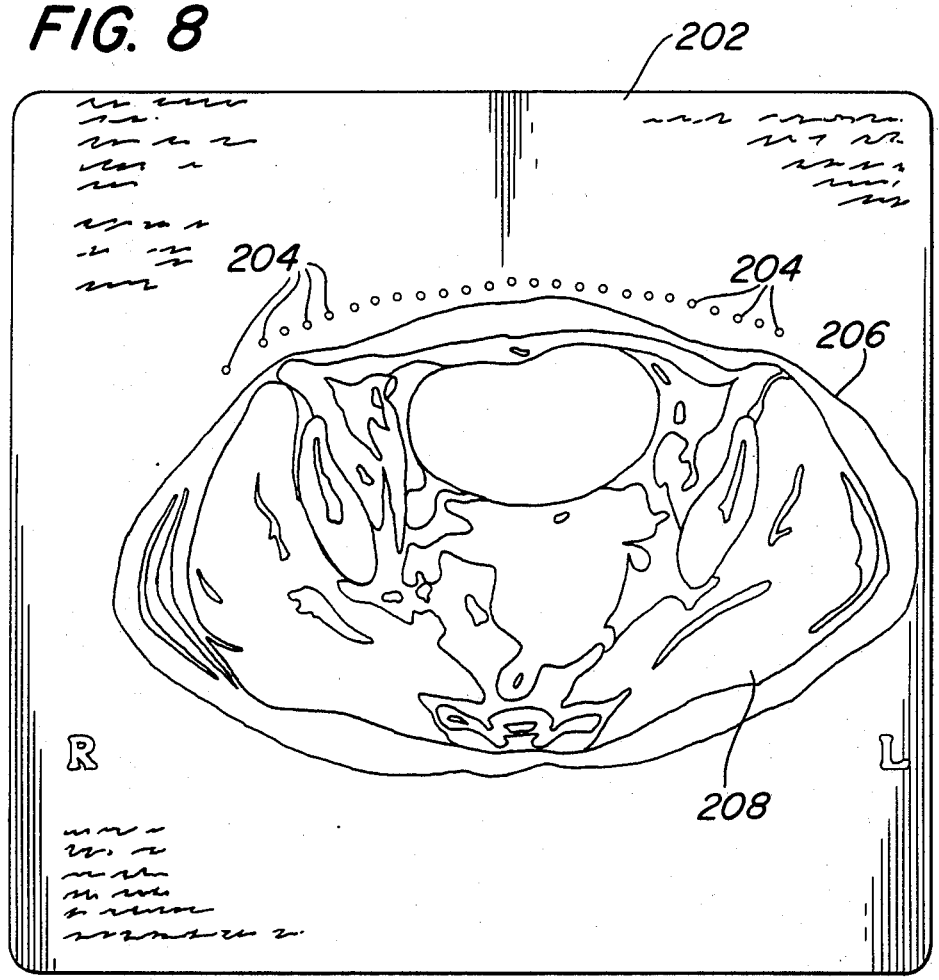
FIG. 8 is a plan view of a developed CT scan film bearing images created by the marker sheet of FIGS. 1 when used on a person.

The embodiment 200 is of particular utility in CT scan applications wherein a transverse image of the body portion being scanned is produced. A representative film 202 showing that image is found in FIG. 8. Thus, as can be seen in that figure the indicia formed by the line pattern 28 of the marker sheet 200 constitutes a series of dots 204 (i.e., the cross section of the radio-opaque material forming the vertical lines 30) disposed over the surface 206 of the transverse section of the body portion 208 scanned. As will be appreciated by those skilled in the art if the transverse (horizontal) lines of the grid-like pattern were also radio-opaque and if the transverse section created by the CT scan was through one of those transverse lines the indicia appearing in the film would be a line, rather than a series of dots 204. Obviously, such a line could not provide the location identification ability of the series of dots.

Figure 4:
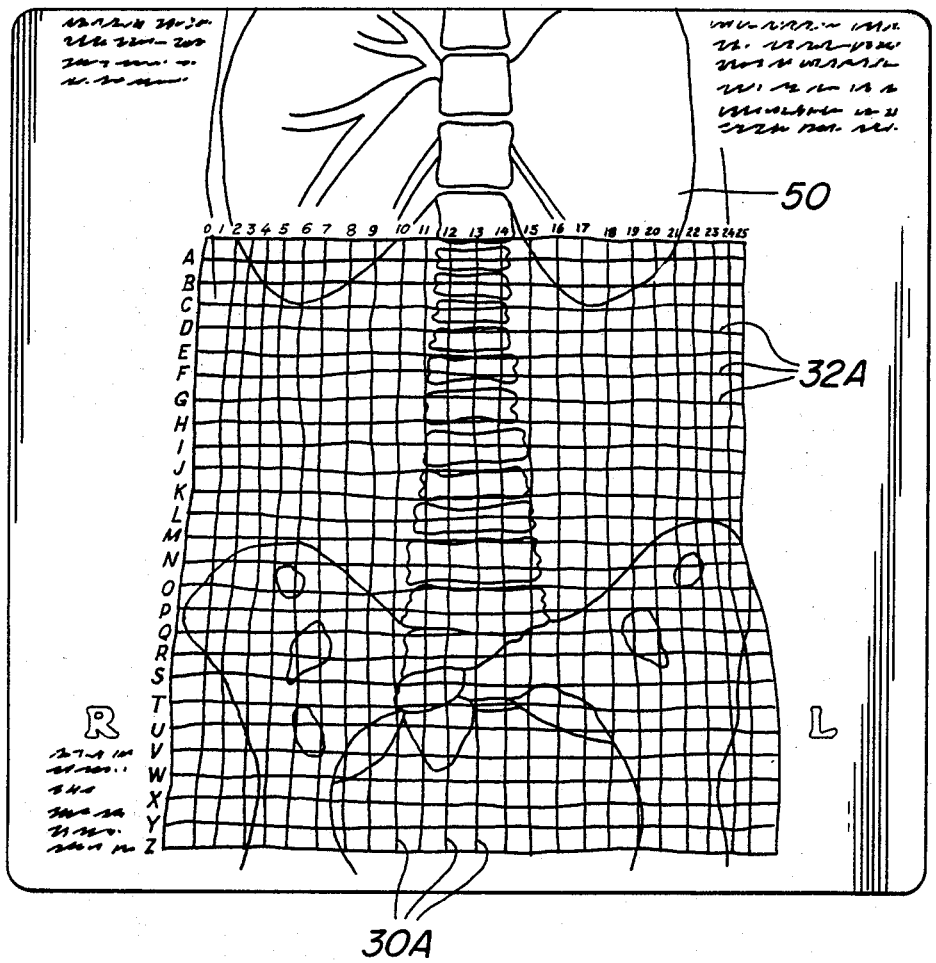
FIG. 4 is a plan view of a developed X-ray film bearing images created by the marker sheet of FIGS. 1 when used on a person.

While not shown herein a plan view scan or X-ray taken using the marker device 200 will produce an image similar to that of FIG. 4, except that the line pattern will not include any transverse lines.

Figure 6:
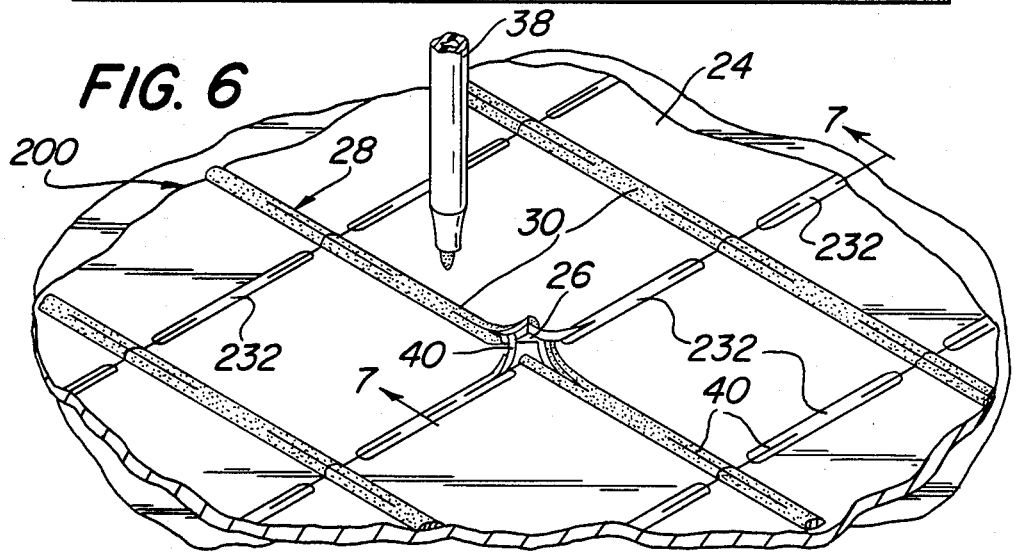
FIG. 6 is an enlarged perspective view of a portion of the marker device shown in FIG. 5 showing one aspect of its manner of use.
Figure 7:
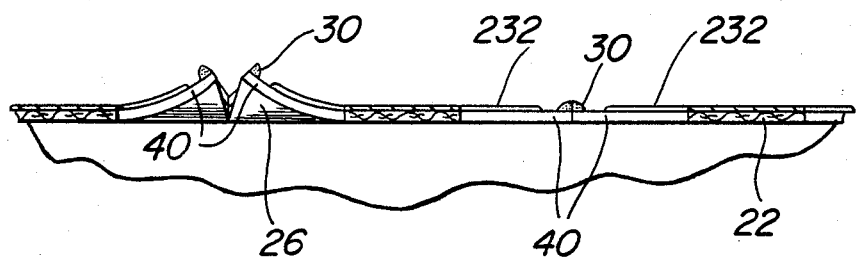
FIG. 7 is an enlarged sectional view taken along line 7—7 of FIG. 6.

As can be seen in FIGS. 6 and 7 the marker sheet 200 includes the heretofore identified die-cut openings 40 at the intersections of the radio-opaque vertical lines 30 and the radio transparent horizontal lines 232. The function of these openings 40 is the same as described heretofore with reference to marker sheet 20.

In accordance with the preferred embodiments of this invention the spacing between all of the lines of the grid-like pattern are the same, except that one end-most vertical line (e.g., the left-most line) be spaced by a greater distance from the immediately adjacent vertical line than the spacing between all the other vertical lines. This feature enables the radiologist to determine the right-left orientation of the radiographic image in the case that the sheet 20 or 200 does not include any other radio-opaque indicia, e.g., words, letters, numbers, etc., which would indicate the film's orientation.

Inasmuch as this invention relates to all types of biological imaging processes it must be understood that the terms "radiographic", "radio-opaque", "radiation", etc. as used in this application are not to limit the invention to any particular imaging methodology.

Without further elaboration the foregoing will so fully illustrate our invention that others may, by applying current or future knowledge, adopt the same for use under various conditions of service.

What we claim is:

1. A device for producing plural linear indicia on a film bearing a radiographic image of a portion of the body of a being over which said device is disposed to facilitate the location of a part of the being's body within said image by reference to said indicia, said device comprising a flexible substrate having indicia producing means located thereon, said indicia producing means producing said desired indicia when said film is exposed to radiation and developed to produce said radiographic image, said indicia producing means comprising carrier means having very fine particles of a radioopaque material disposed therein, said carrier means with said particles therein being applied on said substrate in a first group of plural rows of lines, with the spacing between said lines of said first group being preselected, said substrate including portions located at preselected locations on said lines through which at least one visible indicia mark may be applied onto the portion of the body of the being disposed thereunder.

2. The device of claim 1 wherein each of said substrate portions comprises a respective opening extending through a respective one of said lines, with said openings being at predetermined spacings, said indicia applying means comprising marking means to be inserted through at least a selected one of said openings to apply said visible indicia mark onto the portion of the body of said being which is located under said selected opening.

3. The device of claim 1 additionally comprising means to enable said device to be releasably disposed on a portion of the body of said being during exposure of said film to said radiation.

4. The device of claim 2 additionally comprising means to enable said device to be releasably disposed on a portion of the body of said being during exposure of said film to said radiation.

5. A device for producing plural linear indicia on a film bearing a radiographic image of a portion of the body of a being to facilitate the location of a part of the being's body within said image by reference to said indicia, said device comprising a flexible substrate in the form of a sheet of material which is sufficiently translucent or transparent to enable the portion of the body of said being disposed under said device to be visible therethrough and having indicia producing means located thereon, said indicia producing means producing said desired indicia when said film is exposed to radiation and developed to produce said radiographic image, said indicia producing means comprising carrier means having very fine particles of a radio-opaque material disposed therein, said carrier means with said particles therein being applied on said substrate in a first group of plural rows of lines, with the spacing between said lines of said first group being preselected.

6. The device of claim 5 wherein said substrate comprises spun bonded nylon.

7. The device of claim 5 additionally comprising means to enable said device to be releasably disposed on a portion of the body of said being during exposure of said film to said radiation.

8. The device of claim 5 additionally comprising plural openings in said device, said openings extending through said lines at predetermined spacings, said openings enabling marking means to be inserted through at least a selected one of said openings to apply a mark onto the portion of the body of said being which is located under said selected opening.

9. The device of claim 5 wherein said carrier means with said particles therein is applied on said substrate in a second group of plural rows of lines, with the spacing between said lines of said second group being preselected, said lines of said second group intersecting the lines of said first group to form a grid-like radio-opaque pattern on said substrate.

10. The device of claim 9 additionally comprising plural openings in said device, said openings extending through the intersection of said lines of said first and second groups, said openings enabling marking means to be inserted through at least a selected one of said openings to apply a mark onto the portion of the body of said being which is located under said selected opening.

11. The device of claim 9 additionally comprising means to enable said device to be releasably disposed on a portion of the body of said being during exposure of said film to said radiation.

12. The device of claim 11 additionally comprising means to enable said device to be releasably disposed on a portion of the body of said being during exposure of said film to said radiation.

13. The device of claim 9 wherein said carrier means comprises a plastisol and wherein said particles comprise lead.

14. The device of claim 13 wherein said plastisol with said particles therein initially comprises a slurry which after being applied onto said substrate is cured thereon.

15. The device of claim 9, additionally comprising means to enable said device to be releasably disposed on a portion of the body of said being during exposure of said film to said radiation.

16. The device of claim 9 wherein said substrate comprises spun bonded nylon.

17. The device of claim 1 wherein said carrier means comprises a plastisol and wherein said particles comprise lead.

18. The device of claim 17 wherein said plastisol with said particles therein initially comprises a slurry which after being applied onto said substrate is cured thereon.

19. A device for producing plural linear indicia on a film bearing a radiographic image of a portion of the body of a being to facilitate the location of a part of the being's body within said image by reference to said indicia, said device comprising a flexible substrate having indicia producing means located thereon, said indicia producing means producing said desired indicia when said film is exposed to radiation and developed to produce said radiographic image, said indicia producing means comprising carrier means having very fine particles of a radioopaque material disposed therein, said carrier means with said particles therein being applied on said substrate in respective first and second groups of plural rows of lines, with the spacing between said lines of said first group being preselected, said second group of lines intersecting said first group of lines but being formed of a material which does not produce an image on said film when said film is developed.

20. The device of claim 19 additionally comprising plural openings in said device, said openings extending through the intersection of said lines of said first and second groups, said openings enabling marking means to be inserted through at least a selected one of said openings to apply a mark onto the portion of the body of said being which is located under said selected opening.

21. The device of claim 20 wherein said carrier means comprises a plastisol and wherein said particles comprise lead.

22. The device of claim 19 wherein the spacing between one of the side-most disposed lines of said first group and the immediately adjacent line of said first group is greater than the spacing between the other lines of said first group.

23. The device of claim 22 additionally comprising plural openings in said device, said openings extending through the intersection of said lines of said first and second groups, said openings enabling marking means to be inserted through at least a selected one of said openings to apply a mark onto the portion of the body of said being which is located under said selected opening.

24. The device of claim 23 wherein said carrier means comprises a plastisol and wherein said particles comprise lead.

25. A method of making a device for producing plural linear indicia on a film bearing a radiographic image of a portion of the body of a being to facilitate the location of a part of the being's body within said image by reference to said indicia, said device comprising a flexible substrate in the form of a sheet of material which is sufficiently translucent or transparent to enable the portion of the body of said being disposed under said device to be visible therethrough, said method comprising applying indicia producing means on said substrate, said indicia producing means producing said desired indicia when said film is exposed to radiation and developed to produce said radiographic image, said indicia producing means comprising carrier means having very fine particles of a radioopaque material disposed therein, said carrier means with said particles therein being applied to said substrate in a first group of plural rows of lines, with the spacing between said lines of said first group being preselected, said substrate being formed so that it includes portions located at said lines through which at least one visible indicia mark may be applied onto the portion of the body of the being disposed thereunder.

26. The method of claim 25 wherein said portions are formed as openings in said device, with said openings extending through said lines at predetermined spacings.

27. The method of claim 26 wherein said carrier means with said particles therein is applied on said substrate in a second group of plural rows of lines, with the spacing between said lines of said first second group being preselected, said lines of said second group intersecting the lines of said first group to form a grid-like radio-opaque pattern on said substrate.

28. The method of claim 26 wherein said carrier means comprises a plastisol and wherein said particles comprise lead.

29. The method of claim 28 wherein said plastisol with said particles therein initially comprises a slurry, said method additionally comprising silk screening said slurry onto said substrate and thereafter curing it thereon.

30. The method of claim 26 wherein said carrier means comprises a plastisol and wherein said particles comprise lead.

31. The method of claim 30 wherein said plastisol with said particles therein initially comprises a slurry, said method additionally comprising silk screening said slurry onto said substrate and thereafter curing it thereon.

32. The method of claim 25 wherein said carrier means with said particles therein is applied on said substrate in a second group of plural rows of lines, with the spacing between said lines of said second group being preselected, said lines of said second group intersecting the lines of said first group to form a grid-like radio-opaque pattern on said substrate.

33. The method of claim 32 wherein said carrier means comprises a plastisol and wherein said particles comprise lead.

34. The method of claim 33 wherein said plastisol with said particles therein initially comprises a slurry, said method additionally comprising silk screening said slurry onto said substrate and thereafter curing it thereon.

35. A method of locating a desired part of a being from a radiographic image of a portion of the body of a being containing said desired part comprising applying a marking device over a selected portion of the body said being, said device comprising a flexible substrate in the form of a sheet of material which is sufficiently translucent or transparent to enable the portion of the body of said being disposed under said device to be visible therethrough and having indicia producing means located thereon, said indicia producing means producing said desired indicia when said film is exposed to radiation and developed to produce said radiographic image, said indicia producing means comprising carrier means having very fine particles of a radio-opaque material disposed therein, said carrier means with said particles therein being applied on said substrate in a first group of plural rows of lines, with the spacing between said lines of said first group being preselected, said method additionally comprising disposing a radiosensitive film with respect to said portion of the being's body so that said portion of the being's body is interposed between said marking device and said film, exposing said film to radiation through the device and the portion of the patient's body, and thereafter developing the film so that a plurality of lines are produced over the radiographic image of the portion of the being's body to facilitate the location of said desired part.

36. The method of claim 35 additionally comprising locating said desired part from said image by reference to said lines, and while said marking device is disposed over said being visibly marking the body of the being at the selected location with visible indicia.

37. The method of claim 36 wherein the substrate of the marking device includes plural openings in the lines, and wherein said method additionally comprises inserting a marking instrument through at least one opening adjacent the portion of the image of said selected part to visibly mark the body of the being at the selected location with visible indicia.

* * * * *